United States Patent

Carté et al.

[11] Patent Number: 5,947,917
[45] Date of Patent: Sep. 7, 1999

[54] ADHESIVE BANDAGE OR TAPE

[75] Inventors: Theresa Carté, Wickliffe; Karen Spilizewski, Euclid, both of Ohio; James Bodwell, Boalsburg; Benjamin C. Wiegand, Newtown, both of Pa.

[73] Assignees: Avery Dennison Corporation, Pasadena, Calif.; Johnson & Johnson Consumer Products, Inc., New Brunswick, N.J.

[21] Appl. No.: 09/141,966

[22] Filed: Aug. 28, 1998

[51] Int. Cl.$^6$ ..................................... A61F 13/00
[52] U.S. Cl. .................................. 602/52; 602/58
[58] Field of Search ................... 602/52, 58, 57

[56] References Cited

U.S. PATENT DOCUMENTS

| | | | |
|---|---|---|---|
| 4,090,013 | 5/1978 | Ganslaw et al. | 526/15 |
| 4,812,541 | 3/1989 | Mallya et al. | 526/264 |
| 4,880,416 | 11/1989 | Horiuchi et al. | 604/307 |

*Primary Examiner*—John G. Weiss
*Assistant Examiner*—Kelvin Hart
*Attorney, Agent, or Firm*—Renner, Kenner, Greive, Bobak, Taylor & Weber

[57] ABSTRACT

A water resistant, flexible, dermal adhesive product for conformable topical application to human skin, the dermal adhesive product comprising a backing sheet having an adhesive for removably adhering the sheet to the skin, wherein the adhesive is a highly crosslinked pressure sensitive adhesive composition comprising the polymerization reaction product of about 75% to about 95% of a mixture of at least two alkyl acrylate or methacrylate esters, about 1% to about 10% ethylenically unsaturated carboxylic acid, and about 10% to about 20% vinyl lactam, by dry weight of solids, preferably about 80% to about 90% of a mixture of at least two alkyl acrylate or methacrylate esters, about 2% to about 5% ethylenically unsaturated carboxylic acid, and about 10% to about 20% vinyl lactam, by dry weight of solids.

26 Claims, 1 Drawing Sheet

ADHESIVE BANDAGE OR TAPE

FIELD OF THE INVENTION

The present invention is directed to pressure sensitive adhesive bandages and tapes. More particularly, the present invention is directed to pressure sensitive adhesive bandages, medical tapes and dressings, and the like exhibiting improved flexibility and moisture—or water—resistance performance during active wear.

BACKGROUND OF THE INVENTION

Skin-contact adhesive products, such as bandages, tapes, dressings and the like, generally contain a protective layer, that is, a backing substrate or facestock, and an adhesive to promote adherence of the protective layer to the skin. In order to provide comfort to the wearer of the skin-contact adhesive product, the protective layer, or facestock, has been designed to be flexible and conformable to the skin of the wearer. Adhesives have been formulated which provide adherence of the product to the skin, while still exhibiting the necessary degree of release when intentionally removed so as not to tear the skin which it contacted, and not to leave adhesive residue on the skin after removal. Skin-contact adhesives must also be formulated so as not to contain ingredients which irritate damaged skin or the surrounding healthy skin.

Pressure sensitive adhesive bandages and medical tapes have existed for a long time. Their constructions are similar but differ in that an adhesive bandage normally has a gauze bonded to the adhesive and is protected by a release liner. In addition, adhesive bandages are produced in a greater variety of shapes and sizes than tapes. The adhesives and backing materials for both may be the same, however. Both require the ability to be sterilized without material loss of adhesive properties and it is desirable for the adhesive to be hypoallergenic. This is not a characteristic of natural rubber based adhesives.

A medical tape is typically slit from a roll of a facestock or backing having on at least one surface thereof an adhesive which will adhere to skin under all conditions without irritation, yet will not have an adhesion so great that the tape can be removed only with accompanying discomfort.

Bandages have the same requirement but differ from tapes in that they are die cut to select sizes, with the adhesive being protected by a discardable release liner and a portion of the adhesive surface being bonded to a gauze which covers a wound. Traditionally used adhesives include natural rubber based adhesives which are not hypoallergenic.

One class of adhesive bandage is intended for use by physically or athletically active people. This adhesive bandage is characterized by enhanced flexibility and water resistance, permitting freedom of movement during exercise and resisting peel-off due to skin perspiration or contact with water.

An acceptable adhesive bandage must have a backing material which is flexible yet strong, and an adhesive which is able to be removed without skin irritation, yet tenacious enough to conformably adhere to the skin during movement and when in contact with water or skin perspiration. Additional requirements are aging stability and the capability of being subjected to sterilization procedures without degradation of performance.

The adhesive must exhibit a balance between its shear properties and adhesion, which are inversely related. In a "wet flex" performance test for adhesive bandages, when applied to fingers, the failure modes are "flagging", that is, when the overlapped bandage pops open due to a failure to adhere to itself, and "ring off", when the overlapped bandage loses adhesion to the skin and slips off. Conversely, an adequate degree of shear is required so that no adhesive residue remains when the bandage is removed from the skin of the wearer.

It is therefore an object of the present invention to provide a pressure sensitive adhesive bandage or medical tape which exhibits wet flex characteristics.

It is a further object of the invention to provide a bandage or medical tape which carries a pressure sensitive adhesive exhibiting both good adhesion to self, and no adhesive residue on skin upon removal.

It is a further object of the present invention to provide a pressure sensitive adhesive bandage or medical tape which exhibits aging stability.

It is a further object of the invention to provide an adhesive bandage or medical tape which is capable of being subjected to conventional sterilization techniques without degradation of the adhesive performance.

SUMMARY OF THE INVENTION

The present invention therefore provides a water resistant, flexible, dermal adhesive product for conformable topical application to human skin, the dermal adhesive product comprising a backing sheet having an adhesive for removably adhering the sheet to the skin, wherein the adhesive is a highly crosslinked pressure sensitive adhesive composition comprising the polymerization reaction product of about 75% to about 95% of a mixture of at least two alkyl acrylate or methacrylate esters, about 1% to about 10% ethylenically unsaturated carboxylic acid, and about 10% to about 20% vinyl lactam, by dry weight of solids.

The present invention preferably provides a water resistant, flexible, dermal adhesive product for conformable topical application to human skin, the dermal adhesive product comprising a backing sheet having an adhesive for removably adhering the sheet to the skin, wherein the adhesive is a highly crosslinked pressure sensitive adhesive composition comprising the polymerization reaction product of about 80% to about 90% of a mixture of at least two alkyl acrylate or methacrylate esters, about 2% to about 5% ethylenically unsaturated carboxylic acid, and about 10% to about 20% vinyl lactam, by dry weight of solids.

In a preferred embodiment, the present invention further provides a water resistant, flexible, dermal adhesive product for conformable topical application to human skin, the dermal adhesive product comprising a backing sheet having an adhesive for removably adhering the sheet to the skin, wherein the adhesive is a highly crosslinked pressure sensitive adhesive composition comprising:

the polymerization reaction product of:
a) about 1 to about 5 weight percent acrylic acid;
b) about 80 to about 90 weight percent of a mixture at least two alkyl acrylate or methacrylate esters;
c) about 10 weight percent to about 20 weight percent N-vinyl lactam; and,
an effective amount of a crosslinking agent.

In a preferred embodiment of the invention, the N-vinyl lactam is N-vinyl pyrrolidone. The backing or substrate is preferably a flexible sheet of at least one of polyethylene film, polyurethane film, polyvinylchloride film, polyethylene foam, polyurethane foam, polyvinylchloride foam, and the like.

DETAILED DESCRIPTION OF THE INVENTION

The present invention relates to flexible, dermal adhesive products such as pressure sensitive adhesive bandages, medical tapes, medical dressings, surgical dressings, surgical drapes, and the like, which employ an acrylic based pressure-sensitive adhesive to provide a desired level of aggressive adhesion to skin under moist conditions, in combination with flexibility for conformably responding to body movements of the wearer.

The adhesive has both shear and adhesion properties sufficient to allow a release from the skin without irritation or discomfort, while providing an adhesion to self, and to skin, to prevent flagging and ring off. The adhesive exhibits excellent aging and is not degraded by conventional sterilization procedures.

The improved performance characteristics of the adhesive of the instant invention enables it to be used on any suitably flexible backing or face stock used in bandage and tape construction. Properties induced in the adhesive by the selection of monomers and the use of crosslinking provide excellent moisture resistance.

Figure 1:
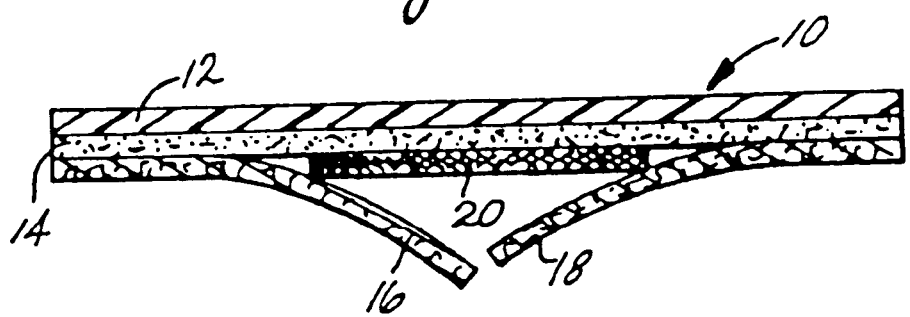
Figure 2:
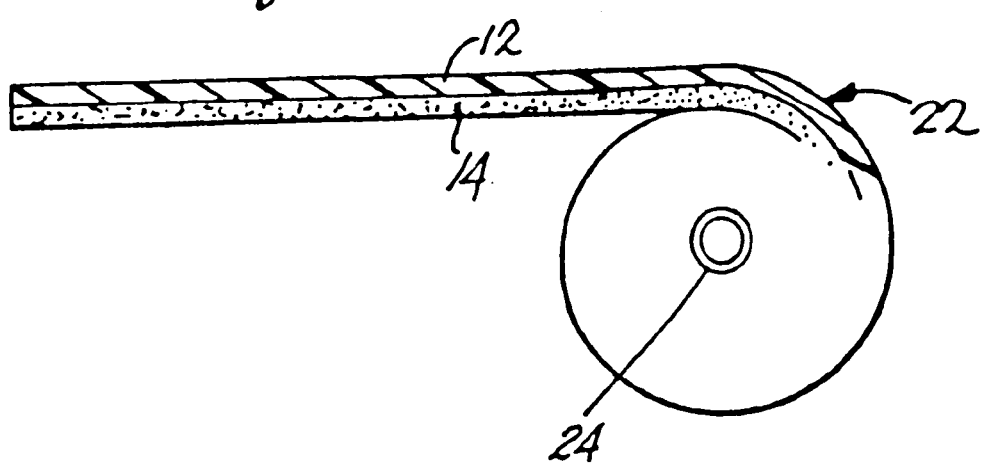

In FIGS. 1 and 2 there are shown typical constructions for an adhesive bandage and a medical tape. With reference to FIG. 1, an adhesive bandage 10 comprises a backing or facestock 12 having coated on one surface thereof a self adhesive or pressure-sensitive adhesive layer 14 which is protected by release liner segments 16 and 18 and which supports an absorbent pad, or gauze 20.

With reference to FIG. 2, a medical tape consists of backing 12 and adhesive 14 wound on a paper spool 24. The medical tape is usually formed in long rolls, slit into individual rolls of tape.

Adhesive bandages come in a variety of configurations depending upon the application to which it will be placed. According to the present invention, the adhesive skin-contact product contains a facestock layer, that is, a backing or substrate, which is water resistant. The preferred backing or substrate material is both conformable to the contours of the body, and flexible so as to permit free movement of the body part wearing the product. Further, the preferred substrate is lightweight, and is preferably elastic (elastomeric) in character. It can be a woven or nonwoven backing, such as a fabric, a film or a foam, preferably about 1 mil to about 30 mils thick. Preferred backing materials include polyolefin (such as polyethylene) film or foam, polyurethane film or foam, and polyvinylchloride film or foam. Other examples of backings include, but are not limited to nonwoven backing materials such as polyurethane or elastomeric polyester materials and the like, or knitted or woven fabrics such as cotton, polyester, rayon and the like.

The backing for the bandage or medical tape may be clear, transparent, or opaque. Normally it has a skin color, but "designer" colors and patterns are becoming popular. It may be solid or porous, permeable or perforated, as adapted for the requirements of the product application, as well as being a function of the composition and form of the backing material.

In a bandage, the absorbent pad or gauze generally occupies a zone smaller than the size of the backing to permit exposed adhesive to secure the pad or gauze to the skin or wound. The gauze is typically cotton and may be coated or laminated to resist bonding to the wound.

All elements of the adhesive product construction, according to the present invention are sterilizable, to avoid infection of the body part to which it is applied. Sterilization may be achieved by exposure to a sterilizing gas such as ethylene oxide or by radiation using actinic or electron beam radiation. Means and conditions for sterilization are disclosed in "Biocompatible Polymers, Metals and Composites" published by Technomic Publishing and edited by M. Szycher Ph.D. In one method, the adhesive bandage and its packaging materials are subjected to sterilization by contact for up to about two hours with ethylene oxide at up to about 180° F.

The preferred embodiment of the present invention is a skin-contact adhesive bandage, for which its conformability to the contours of the body and flexibility with body movement characteristics are most advantageous. However, the invention includes medical tape, and medical or surgical dressings for which these characteristics provide comfort for the wearer. The present invention is also applicable to adhesive medical products, such as dressings which are used for the long term (such as that used with an ostomy bag appliance).

The adhesive utilized in the adhesive skin-contact product is an acrylate or methacrylate based pressure sensitive adhesive, most preferably a solvent based acrylate adhesive. The adhesive is prepared according to standard industry procedures.

The adhesive is preferably a polymerization reaction product of at least two alkyl acrylate or methacrylate ester monomers, at least one ethylenically unsaturated carboxylic acid, at least one vinyl lactam, and most preferably including a crosslinking agent. Examples of suitable alkyl acrylate or methacrylate esters include, but are not limited to, butyl acrylate, ethyl acrylate, 2-ethylhexyl acrylate, isooctyl acrylate, isononyl acrylate, isodecyl acrylate, methyl acrylate, methylbutyl acrylate, 4-methyl-2-pentyl acrylate, sec-butyl acrylate, ethyl methacrylate, isodecyl methacrylate, methyl methacrylate, and the like, and mixtures thereof.

Examples of suitable ethylenically unsaturated carboxylic acids include, but are not limited to, acrylic acid, methacrylic acid, fumaric acid, itaconic acid, and the like, and mixtures thereof. A preferred ethylenically unsaturated carboxylic acid monomer is acrylic acid.

Examples of suitable vinyl lactams include, but are not limited to, N-vinyl caprolactam, 1-vinyl-2-piperidone, 1-vinyl-5-methyl-2-pyrrolidone, N-vinyl pyrrolidone, and the like, and mixtures thereof. The components are generally present in an amount of about 75% to about 95% alkyl acrylate or methacrylate ester, about 1% to about 10% ethylenically unsaturated carboxylic acid, and about 10% to about 20% vinyl lactam, by dry weight solids. The components are preferably present in an amount of about 80% to about 90% alkyl acrylate or methacrylate ester, about 2% to about 5% ethylenically unsaturated carboxylic acid, and about 10% to about 20%, most preferably about 15% to about 20%, vinyl lactam, by dry weight solids.

In one preferred embodiment, the polymerization reaction product comprises a) about 50 to about 70 weight percent solids of 2-ethylhexylacrylate, b) about 15 to about 25 weight percent solids of butylacrylate, c) about 1 to about 5 weight percent solids of acrylic acid, and d) about 10 to about 20 weight percent solids of N-vinylpyrrolidone.

Optionally, an additional polymerizable monomer can be included in the polymerization product, such as a hydroxy acrylate ester, including but not limited to hydroxyethyl acrylate and hydroxypropyl acrylate, in an amount of 0 to about 10% by weight, preferably about 1% to about 4%.

The polymerization product generally has a weight average molecular weight of about 150,000 to about 400,000, preferably about 200,000 to about 300,000. The polymerization product is preferably dissolved in at least one organic solvent for application to the backing substrate, such as acetone, ethyl acetate, toluene, xylene, and the like. Other solvents can be added to control viscosity and rheology of the polymerization product solution, including but not limited to hexane, heptane, isopropanol, and methanol.

The polymerization product may be crosslinked to the desired extent, prior to use, using heat, ionic additives, actinic or electron beam radiation and the like. Any suitable polyvalent metal oxide or salt is useful as a crosslinking agent, but preferred crosslinkers are selected from the group consisting of oxides or salts of aluminum, calcium, chromium, iron, magnesium, zinc, and mixtures thereof. A preferred class includes for example, aluminum acetate, alum acetylacetonate, zinc oxide, and the like.

Another type of crosslinking agent is a multi-ethylenically unsaturated compound, such as ethylene glycol dimethacrylate, methylene-bis-acrylamide, and the like. The crosslinking agent is optionally present in an amount sufficient to effect the crosslinking of the adhesive formulation polymerization product upon exposure to heat or UV light, as is known in the art, preferably in an amount up to about 1% by weight of the adhesive components, most preferably about 0.05% to about 0.5% by weight.

Other conventional components can be added to the adhesive of the present invention, such as by being added to the solution of the polymerization product and crosslinker (if any), including but not limited to inhibitors, fillers, pigments, stabilizers, tackifiers, UV absorbers, and the like.

The above pressure sensitive adhesive product, according to the present invention, is compatible with human skin, even during extended contact, and is both flexible and conformable. It exhibits sufficient adhesion, or bonding strength, to prevent peeling of the adhesive product from the skin prematurely, but is not so tenacious as to damage or irritate the skin during removal, especially sensitive skin, or to leave adhesive residue on the skin (thus exhibiting acceptable shear properties). The adhesive of the present invention exhibits sufficient adhesion to the substrate material to prevent unwrapping of the adhesive product during wear, such as when a bandage is wrapped upon itself on a finger.

In one embodiment, the adhesive skin-contact product of the present invention may be made by coating the adhesive onto a liner, and then transferring (laminating) the adhesive onto the substrate, backing material. The liner (such as a heavy kraft paper, on the order of about 60 pounds per ream of paper), is coated on one side with a release layer, such as a silicone compound, and is then coated in a first stage, with the adhesive on top of the release layer. The adhesive can be applied to the liner as a solution or emulsion of the adhesive formulation, from which the solvent or water is removed by heating, or as a hot melt adhesive such as by casting or extrusion.

The facestock, (backing or substrate) is then laminated to the adhesive layer, in a second stage. If the backing is formed on a carrier, the backing/carrier laminate is contacted with the adhesive/liner laminate, such that the backing is interposed between its carrier on one side, and the adhesive layer of the adhesive coated liner on the other side. The carrier is then stripped off of the laminate, and is discarded, thereby leaving a laminate of backing, adhesive and release liner.

Alternatively, the adhesive skin contact product of the present invention may be made by forming the backing material onto a carrier-borne adhesive, as described in U.S. Ser. No. 09/094,767, incorporated herein by reference.

If the laminate is to be converted to an adhesive bandage or wound dressing, the rolled sheet may be perforated (such as being rolled with pins) and then is cut to size, in one application on the order of 3¼ inches wide, although the width could vary. The length of the bandage, is thereafter cut from the width of the roll, in a third stage. The narrow laminate is conventionally wound in large rolls, for delivery to another apparatus.

In the third stage, the heavy liner is stripped off the narrow laminate. The adhesive sticks to the backing, but not the liner. Simultaneously, a lightweight paper liner is contacted with the laminate, (in the case of a bandage, a gauze or an adsorbent pad may first be applied to the adhesive, and the liner comprising two overlapping pieces to form the "pull tab" are laminated), and then the new laminate is passed to a cutter, or a die, to cut the bandage to the desired width.

After converting the laminated facestock to the bandage, the bandages or tapes are packaged and sterilized.

SPECIFIC EMBODIMENTS OF THE INVENTION

By way of exemplification, but not limitation, of the present invention, adhesive bandages were prepared having a perforated polyvinylchloride foam backing layer for added comfort, approximately 20 mils thick, and a solvent based acrylic pressure sensitive adhesive comprising the polymerization product of a formulation of n-butylacrylate, 2-ethylhexyl acrylate, acrylic acid, N-vinyl pyrrolidone; and, a crosslinker. The adhesive bandages were subjected to a sterilization procedure, being contacted for up to two hours with ethylene oxide at a temperature of at least 180° F.

The resulting adhesive bandages were tested according to the test protocols described below for wear, trans epidermal water loss, and adhesion. The results of the testing are reported, in Tables I–III below.

Wet Wear Test

This protocol defines a method to evaluate the overlap adhesion properties of experimental adhesive bandages when applied to the fingers of random test subjects and then soaked in detergent water for one or more 15 minute cycles.

Procedure

1. Each test subject is selected in a blinded, controlled, randomized manner.
2. Coded adhesive bandages are randomly applied in a rotational arrangement to the first joint of the first, second and third fingers of each hand, depending on the number of samples being tested. The absorbent pad will be on the palmar side of the finger, with the overlap of the adhesive tabs on the knuckle.
3. Test subjects will wait one full minute, and then immerse their hands in a solution of 60 ml of Ivory liquid detergent per gallon of water (temperature 105–110° F.).
4. Test subjects are instructed to flex their fingers continuously for 15 minutes in the solution.
5. At the end of the 15 minute immersion in the detergent solution, the test subjects are instructed to pat-dry their hands with a paper towel.
6. The overlap adhesion is then read using the scale shown below, and the test articles will be removed from the fingers of the test subjects.

Overlap Adhesion Scale

0=OFF Completely.

1=Hanging—pad away from the skin, and between ¼ and ¾ of the adhesive tab is off.

2=Hanging—pad away from the skin, and ¼ of the adhesive tab is off.

3=Pad in contact with skin, but more than ¾ of overlap is up.

4=Pad in contact with skin, but between ¼ and ¾ of overlap is up.

5=Overlap is up approximately ¼.

6=Overlap is up slightly.

7=Perfect adhesion.

An OFF sample is recorded as a failure ("0"), but a note is made on the data sheet to indicate whether it is a "ring-off" or an overlap failure. If the former, the bandage will be graded for overlap adhesion according to the above scale, and this score will be recorded above the "0" on the data sheet.

Mass Transfer

Mass transfer may be observed after the removal of the test articles from the fingers of the test subject. Mass transfer indicates the amount of adhesive residue left on the finger of the test subject after removal of the test article. Mass transfer observed for the adhesives tested is reported below as a percentage of test subjects exhibiting mass transfer of adhesive residue during the study.

Trans Epidermal Water Loss Test (Tape Trauma/Skin Irritation)

The Trans Epidermal Water Loss protocol is a method to evaluate skin irritation caused by "tape trauma" resulting from the repeated application of adhesive bandages to the upper backs or volar forearms of volunteer test subjects. Instrumental assessments of the rate of transepidermal water loss on the test sites are measured by a Servomed Evaporator.

Instrumentation

Servomed Evaporator—The evaporimeter is a noninvasive measurement which measures the amount of transepidermal water loss (TEWL) from the skin. Increases in TEWL scores are caused by removal of stratum corneum, because the probe is in contact with the deeper skin layers. The more stratum corneum the adhesive bandage removes, the higher the TEWL score should be.

To obtain transepidermal water loss measurements, the probe of the evaporimeter will be positioned on an area where an adhesive bandage will be placed to obtain a baseline TEWL score. Readings will be taken where the adhesive portion of the adhesive bandage contacts the skin. No readings will be taken underneath the pad area. Another TEWL measurement will be taken from just outside the test area to obtain a baseline control score. Baseline TEWL readings cannot exceed 7.5 gm/m$^2$ hr for the test subject to be accepted into the study.

Procedure

1. The test subjects will be selected in a blinded, controlled and randomized manner.

2. On day 0, the upper back or volar forearm of the test subject will be inspected for any skin disorders or excessive hair growth.

3. The test sites will be delineated with a surgical marker.

4. Each test subject will be required to acclimate to the conditions of the room for a period of thirty minutes before taking baseline instrumental measurements.

5. Once acclimated, the test subjects are asked to lie prone or sit and water loss measurements are obtained from the proposed test sites.

6. Once baseline instrumental measurements have been obtained, adhesive bandages will be placed on the upper back or volar forearm of the test subjects. Subjects are reminded about restrictions on bathing, swimming and excessive exercising.

7. Test subjects return to the clinic at twenty-four hour intervals over the next four days.

8. Each day, the test products are removed beginning with the outer edge, stopping in the center, and then quickly pulling off the inner edge of the bandage.

9. Any unusual skin irritation observed after removal of the test product is documented indicating the number of occurrences and the severity (slight, moderate, severe).

10. Test subjects will acclimate to the room conditions for thirty minutes.

11. Once acclimated, test subjects will lie in the prone position on an examination table and two chromameter measurements will be obtained from the two areas where the adhesive backing tabs were placed and two readings from outside the test area will be taken from both treatment sites.

12. One TEWL measurement will be obtained from outside the test area from both treatment sites.

13. Bandages will be reapplied daily over the next three days with the last application on day 3, and the last TEWL reading taking place on day 4.

90 Degree Peel Adhesion (Test)

This protocol defines a method of removing a pressure sensitive adhesive tape from a test surface using a 90 degree peeling angle. The test applies to the force required to remove a pressure sensitive adhesive sample at 90 degrees after application to a test surface.

Equipment

1. Instron Tensile Tester.

2. Standard PSTC 2"×6"×$\frac{1}{16}$" stainless steel test panel(s).

3. Dispensing system for solvents, such as contamination-free bottles or stainless steel cans.

4. Absorbent lint-free cleaning material.

5. 1"×8" rectangular mallet-type die cutter and mallet.

6. PSTC mechanical rolldown machine with rubber covered roller(s).

7. A jig or fixture permitting the panel to move freely in a horizontal direction as test sample is removed at a 90 degree angle.

8. Acetone or toluene (reagent or analytical grade).

9. n-Heptane (reagent or analytical grade).

Procedure

1. Condition uncut samples for 24 hours at 73.4 deg. F. (+/−3.6 deg. F.) & 50% RH (+/−2% RH).

2. Die cut required amount of 1"×8" samples in machine direction.

3. Verify accuracy of equipment.

4. Set crosshead speed at 12" (+/−0.5") per minute.

5. Set chart speed at 2" per minute.

6. Set load scale at 10 lbs.

7. Secure horizontal jig in lower jaw of Instron tensile tester.

8. Before each test:

(a) Clean stainless steel panel(s) with:

(b) Acetone or toluene (flood panel).

(c) Heptane (flood panel and use a separate cleaning tissue each time).

(d) Allow 2 minutes to elapse between final heptane wash and sample testing.

9. Peel liner approximately 4" from end of test sample (avoid contacting either adhesive or panel).

10. Lightly apply exposed adhesive sample to test panel (center sample with its length parallel to length of panel).

11. Roll down sample:
   (a) At rate of 12" per minute, using a 4.5# roller.
   (b) Applying no pressure on sample other than roller weight.

If using an automatic rolldown machine; roll once in each direction. If using a hand roller; roll 5 times in each direction. If air bubbles become entrapped, discard sample and prepare new one.

12. Insert panel into horizontal jig (crosshead to be positioned so the upper jaw is approximately 3" from surface of test panel).

13. Insert free end of sample into upper jaw.

14. Turn on chart recorder.

15. Activate crosshead.

16. Record:
   (a) Average peel adhesion value to nearest chart division.
   (b) Failure mode.
   (c) Disregard values obtained first and last ½" of peel.

In case of jerky detachment; record minimum and maximum adhesion values. Note any deviations from standard conditions, sample preparation, conditioning, dwell time, or other test procedure instructions.

17. When testing is completed:
   (a) Clean panels with heptane.
   (b) Store panels away from direct contact with objects which could scratch test surfaces.

180 Degree Peel Adhesion (Test)

This protocol defines a method of removing a pressure sensitive adhesive tape from a test surface using a 180 degree peeling angle. The test applies to the force required to remove a pressure sensitive adhesive sample at 180 degrees after application to a test surface.

The equipment and procedure used in this protocol is the same as in the 90 degree peel adhesion test, except that the horizontal jig is omitted (item 7 of each). Also in the procedure for the 180 degree adhesion test, steps 12 and 13 are modified as follows.

12. Insert bottom edge of test panel into lower jaw of Instron tensile tester (crosshead to be positioned so the upper jaw is approximately 5 inches from lower jaw).

13. Double back free end of sample, and insert into upper jaw. (Be sure both jaws are properly aligned).

Initial examples were tested for peel strength by the 180 degree protocol, but it was found that the better the adhesion, the greater the tendency for the sample to tear. Later samples were tested at 90 degrees for peel strength.

EXAMPLE 1

An adhesive according to the present invention was compounded by introducing about 84 parts by weight of a base polymerization product of the following formulation into about 13 parts by weight toluene solvent with high speed mixing, and a solution of about 0.3 parts by weight crosslinker (aluminum acetylacetonate) and about 0.7 parts inhibitor (2,4 pentanedione) in about 2 parts toluene was added with additional mixing until a uniform consistency was achieved, in order to provide an adhesive having a high degree of crosslinking. The polymer formulation was 60% 2-ethylhexyl acrylate, 20% butylacrylate, 2% acrylic acid, and 18% N-vinyl pyrrolidone by dry weight solids. The resulting adhesive was solvent-coated on a release carrier, was laminated onto a 20 mil polyvinyl chloride foam, and was thereafter converted to bandages. The adhesive bandages were tested according to the above test protocols, and the results of the above tests are reported in Tables I–III below.

COMPARATIVE EXAMPLE 2

Polyvinyl chloride foam bandages were produced, having an acrylate based adhesive formulated with vinyl acetate, but without N-vinyl pyrrolidone. The adhesive bandages were tested according to the above test protocols, and the results of the above tests are reported in Tables I–II below.

EXAMPLE 3

Polyvinyl chloride foam bandages were produced, having an adhesive prepared according to the above procedure of Example 1, except that the base polymer contained 4% acrylic acid, by dry weight solids. The adhesive bandages were tested according to the above test protocols, and the results of the above tests are reported in Tables I–II below.

COMPARATIVE EXAMPLE 4

Polyvinyl chloride foam bandages were produced, having an adhesive prepared according to the above procedure of Example 1, except that the base polymer contained only 9% N-vinyl pyrrolidone, by dry weight solids. The adhesive bandages were tested according to the above test protocols, and the results of the above tests are reported in Tables I–II below.

EXAMPLE 5

Polyvinyl chloride foam bandages were produced, having an adhesive prepared according to the above procedure of Example 1, except that 0.10 parts by weight crosslinking agent was used in the adhesive mixture. The adhesive bandages were tested according to the above test protocols, and the results of the above tests are reported in Tables I–II below.

EXAMPLE 6

Polyvinyl chloride foam bandages were produced, having an adhesive prepared according to the above procedure of Example 1, in which 1 weight % zinc oxide was incorporated into the base polymer of the adhesive. The adhesive bandages were tested according to the above test protocols, and the results of the above tests are reported in Tables I–II below.

EXAMPLE 7

Polyvinyl chloride foam bandages were produced, having an adhesive prepared according to the above procedure of Example 1, having additionally an incorporated monomer of hydroxypropyl acrylate of 2 weight % in the base formulation. The bandages were tested according to the above test protocols, and the results of the above tests are reported in Tables I–II below.

TABLE I

Wet Wear Results

| Example No. | Wet Wear Test (0–7 scale) | Mass Transfer (%)* |
|---|---|---|
| 1 | 6.96 | 0 |
| 2C | 6.88 | no data |
| 3 | 6.83 | 0 |
| 4C | 0.05 | 1 |
| 5 | 7.0 | 4 |
| 6 | 7.0 | 33 |
| 7 | 5.68 | 0 |

*Percentage of participants exhibiting mass transfer.

The adhesive products of the present invention exhibited excellent wet wear characteristics, as demonstrated in the tests results reported in Table I. Overlap adhesion as measured in the Wet Wear Test was near or at the perfect score of 7.0 for the adhesive products of the present invention. The failure mode changed from an overlap failure as observed with current adhesives, that is, where the overlapping area flags and the bandage unwraps, to a ring-off, where the overlap area remains intact, and the bandage slides off the finger. Very few failures of this type were observed for the inventive product in the wet wear test. Comparative Example 4, containing a reduced amount of N-vinyl pyrrolidone, exhibited very poor adhesion in the wet wear test.

Overlap adhesion was also tested by the physical test method, adhesion to self (180 degree peel test). In this test method, an adhesive—backing laminate sample is placed on a stainless steel panel with the adhesive contacting the steel, a second laminate sample is then applied with the adhesive layer contacting the backing layer of the first sample, and the second laminate is then rolled down onto the previously applied first laminate. The force required to remove the top laminate sample from the bottom laminate sample is measured. A test value greater than 5 oz./in. is acceptable, but the higher the adhesion value, the better for adhesive bandages and medical tapes. As reported in Table II, the adhesive products of the present invention exhibited excellent adhesion to self. Each sample performed better than the conventional acrylic adhesive product, and the worse performing sample was Comparative Example 4, having a low N-vinyl pyrrolidone level.

The degree of shear exhibited by the adhesive products of the present invention is shown by their ability to be removed from the skin with little or no mass transfer of adhesive residue (Table I).

The adhesive product of the present invention exhibits enhanced stability as compared to both the conventional acrylic adhesive (2C) and the comparative low N-vinyl pyrrolidone sample (4C). As shown in Table II, the adhesion (oz./in.) of the inventive products is stable over the long term. The closer the aged (4 week) adhesion number is to the initial adhesion number, the more stable the adhesive.

The inventive examples exhibit little degradation over the test period, while the conventional acrylic adhesive failed by splitting during the test, and the low N-vinyl pyrrolidone sample exhibited about half of its already low initial adhesion value after four weeks.

While not wishing to be bound by theory, the stability of the inventive adhesive products may be due to crosslinking in the adhesive which, in part, prevents plasticizer migration from the adjacent backing member. Another benefit of the high degree of crosslinking is the lack of mass transfer of the adhesive to the skin. It is unexpected, however, that in spite of the degree of crosslinking, adhesion to self and wear performance remains high for the inventive adhesive product.

TABLE II

Stability: Adhesion To Self & Stainless Steel

| | 180 Deg. | STABILITY: Adhesion to Stainless Steel (oz/in) | | |
|---|---|---|---|---|
| | Adh. | | 4 weeks | |
| Example No. | to Self (oz/in) | Initial | Rm. Temp | 158° F. |
| 1 | 44.7 | 23.9 | 15.4 | 20.3 |
| 2C | 10.7 | 32.9 | 19.0 | 56.6* |
| 3 | 13.9 | 17.9 | 16.4 | 12.8 |
| 4C | 3.1 | 7.83 | 6.1 | 4.0 |
| 5 | 26.5 | 17.5 | 14.9 | 10.5 |
| 6 | 32.3 | 19.0 | 15.1 | 11.4 |
| 7 | 12.4 | 16.1 | 13.0 | 9.6 |

*Adhesive split.

The adhesive product of Example 1 and Comparative Example 2 were tested for Moisture Vapor Transmission Rate (MVTR) by the technique according to ASTM F-1249, at 100° F., and 100% Relative Humidity (RH) over a 5 cm$^2$ area. The conventional acrylic adhesive exhibited an MVTR of 735±8 g/m$^2$/day, while the inventive product exhibited an improved MVTR of 791±29 g/m$^2$/day.

An unexpected result shown by the testing of the adhesive product of the present invention was revealed by the trans epidermal water loss test. Usually, when an adhesive is modified to be more aggressive and adhesion improves, the adhesive exhibits a corresponding increase in skin irritation. The adhesive products of the present invention, however, actually exhibit a decreased irritation as demonstrated by the above described test, as reported below in Table III. An adhesive bandage according to the present invention, as prepared according to Example 1, was compared in the "TEWL" test to a bandage prepared using a commercial adhesive (Comparative Example 8C) and to a commercial adhesive bandage product (Comparative Example 9C).

TABLE III

Trans Epidermal Water Loss

| Example No. | TEWL (gm/m$^2$/hr) | | |
|---|---|---|---|
| | Day 1 | Day 2 | Day 3 |
| 1 | 0 | 0.822 | 0.061 |
| 8C | 0.5893 | 2.505 | 3.026 |
| 9C | 0 | 1.501 | 0.727 |

The lower the Trans Epidermal Water Loss ("TEWL") value, defined as grams of water lost per square meter per hour, the better the performance (less irritation) of the tested adhesive or adhesive product. The adhesive bandage of Example 1 according to the present invention, exhibited a lower TEWL value initially, essentially zero, as compared to a bandage bearing the commercial adhesive of Example 8C, and much lower second day and third day TEWL values as compared to both Example 8C and the commercial adhesive bandage product of Example 9C.

The present invention thus provides a water resistant, topical, dermal adhesive product including a pressure sensitive adhesive for removably adhering the product to human skin, which product is flexible and conformable, and is comfortable to the wearer. The dermal adhesive product exhibits wet flex characteristics, and exhibits excellent adhesion to self even in moist conditions, while having adequate shear to avoid transfer of adhesive residue to the skin upon removal.

The dermal adhesive product, including the pressure sensitive adhesive, is capable of being sterilized by contact for up to two hours with ethylene oxide at up to 180° F. without deleterious effects on end use performance, and is not adversely affected by aging of the product.

Thus, the objects of the invention are accomplished by the present invention, which is not limited to the specific embodiments described above, but which includes variations modifications and equivalent embodiments defined by the following claims.

We claim:

1. A water resistant, flexible, dermal adhesive product for conformable topical application to human skin, the dermal adhesive product comprising a backing sheet having an adhesive for removably adhering the sheet to the skin, wherein the adhesive is a highly crosslinked pressure sensitive adhesive composition comprising the polymerization reaction product of about 75% to about 95% of a mixture of at least two alkyl acrylate or methacrylate esters, about 1% to about 10% ethylenically unsaturated carboxylic acid, and about 10% to about 20% vinyl lactam, by dry weight of solids.

2. The adhesive product of claim 1, wherein the adhesive is a highly crosslinked pressure sensitive adhesive composition comprising the polymerization reaction product of about 80% to about 90% of a mixture of at least two alkyl acrylate or methacrylate esters, about 2% to about 5% ethylenically unsaturated carboxylic acid, and about 10% to about 20% vinyl lactam, by dry weight of solids.

3. The adhesive product of claim 1, wherein the alkyl acrylate or methacrylate esters are selected from the group consisting of butyl acrylate, ethyl acrylate, 2-ethylhexyl acrylate, isooctyl acrylate, isononyl acrylate, isodecyl acrylate, methyl acrylate, methylbutyl acrylate, 4-methyl-2-pentyl acrylate, sec-butyl acrylate, ethyl methacrylate, isodecyl methacrylate, methyl methacrylate, and mixtures thereof.

4. The adhesive product of claim 1, wherein the ethylenically unsaturated carboxylic acids is selected from the group consisting of acrylic acid, methacrylic acid, fumaric acid, itaconic acid, and mixtures thereof.

5. The adhesive product of claim 1 wherein the vinyl lactams are selected from the group consiting of N-vinyl caprolactam, 1-vinyl-2-piperidone, 1-vinyl-5-methyl-2-pyrrolidone, N-vinyl pyrrolidone, and mixtures thereof.

6. The adhesive product of claim 5 containing about 15% to about 20% vinyl lactam, by dry weight of solids.

7. The adhesive product of claim 6 wherein the vinyl lactam comprises N-vinyl pyrrolidone.

8. The adhesive product of claim 1, wherein the polymerization reaction product additionally comprises up to about 10% by dry weight solids of a polymerizible monomer selected from hydroxyethyl acrylate and hydroxypropyl acrylate.

9. The adhesive product of claim 1, wherein the polymerization reaction product additionally comprises from about 1% to about 4% by dry weight solids of a polymerizible monomer selected from hydroxyethyl acrylate and hydroxypropyl acrylate.

10. The adhesive product of claim 1, wherein the backing sheet is at least one of polyethylene film, polyurethane film, polyvinylchloride film, polyethylene foam, polyurethane foam, polyvinylchloride foam, nonwoven polyurethane, nonwoven elastomeric polyester, knitted fabric, and woven fabric.

11. The adhesive product of claim 1 wherein the mixture of alkyl acrylate esters contains at least butylacrylate and ethylhexylacrylate, the carboxylic acid is acrylic acid, and the vinyl lactam is N-vinyl pyrrolidone.

12. The adhesive product of claim 11 wherein the backing sheet is a perforated polyvinylchloride foam.

13. The adhesive product of claim 1 wherein the sheet is at least one of a pressure sensitive adhesive bandage, a medical tape, a medical dressing, a surgical dressing, a surgical drape, and athletic tape.

14. A water resistant, flexible, dermal adhesive product for conformable topical application to human skin, the dermal adhesive product comprising a backing sheet having an adhesive for removably adhering the sheet to the skin, wherein the adhesive is a highly crosslinked pressure sensitive adhesive composition comprising:

the polymerization reaction product consisting essentially of:
 a) about 1 to about 5 weight percent acrylic acid,
 b) about 80 to about 90 weight percent of a mixture at least two alkyl acrylate esters,
 c) about 10 weight percent to about 20 weight percent N-vinyl lactam; and,
an effective amount of a crosslinking agent.

15. The adhesive product of claim 14, wherein the alkyl acrylate or methacrylate esters are selected from the group consisting of butyl acrylate, ethyl acrylate, 2-ethylhexyl acrylate, isooctyl acrylate, isononyl acrylate, isodecyl acrylate, methyl acrylate, methylbutyl acrylate, 4-methyl-2-pentyl acrylate, sec-butyl acrylate, ethyl methacrylate, isodecyl methacrylate, methyl methacrylate, and mixtures thereof.

16. The article of claim 14 wherein the mixture of alkyl acrylate esters contains at least butylacrylate and ethylhexylacrylate.

17. The adhesive product of claim 16 wherein the ratio of butylacrylate to ethylhexylacrylate is about 1:3.

18. The adhesive product of claim 14 wherein the N-vinyl lactam is selected from the group consisting of N-vinyl caprolactam, 1-vinyl-2-piperidone, 1-vinyl-5-methyl-2-pyrrolidone, N-vinyl pyrrolidone and mixtures thereof.

19. The adhesive product of claim 14 wherein the N-vinyl lactam comprises N-vinylpyrrolidone.

20. The adhesive product of claim 14, wherein the N-vinyl lactam is highly crosslinked with the acrylic, acrylate or methacrylate functionalities.

21. The adhesive product of claim 14 wherein the reaction product comprises:
 a) about 50 to about 70 weight percent solids of 2-ethylhexylacrylate,
 b) about 15 to about 25 weight percent solids of butylacrylate,
 c) about 1 to about 5 weight percent solids of acrylic acid, and
 d) about 10 to about 20 weight percent solids of N-vinylpyrrolidone.

22. The adhesive product of claim 14 wherein the reaction product comprises:
 a) about 60 weight percent solids of 2-ethylhexylacrylate,
 b) about 20 weight percent solids of butylacrylate,
 c) about 2 weight percent solids of acrylic acid, and
 d) about 18 weight percent solids of N-vinylpyrrolidone.

23. The adhesive product of claim 14 wherein the crosslinking agent is alum acetyl acetonate.

24. The adhesive product of claim 14 wherein the sheet is at least one of polyethylene film, polyurethane film, polyvinylchloride film, polyethylene foam, polyurethane foam, polyvinylchloride foam, nonwoven polyurethane, nonwoven elastomeric polyester, knitted fabric, and woven fabric.

25. The adhesive product of claim 14 wherein the sheet is a perforated polyvinylchloride foam.

26. The adhesive product of claim 14 wherein the sheet is at least one of a pressure sensitive adhesive bandage, a medical tape, a medical dressing, a surgical dressing, a surgical drape, and athletic tape.

* * * * *